United States Patent [19]

Spector

[11] Patent Number: 5,631,717
[45] Date of Patent: May 20, 1997

[54] LENSLESS SAFETY SUNGLASSES

[76] Inventor: Donald Spector, 380 Mountain Rd., Union City, N.J. 07080

[21] Appl. No.: 685,410

[22] Filed: Jul. 24, 1996

[51] Int. Cl.$^6$ .............................. G02C 7/10; G02C 7/16
[52] U.S. Cl. .................................. 351/44; 351/46; 2/433
[58] Field of Search ................................ 351/41, 44, 46; 2/431, 432, 433, 15

[56] References Cited

U.S. PATENT DOCUMENTS 5,488,510  1/1996  Lemay .................................. 351/46 X

*Primary Examiner*—Huy Mai
*Attorney, Agent, or Firm*—Michael Ebert

[57] ABSTRACT

Lensless safety sunglasses formed of fabric material die cut or otherwise contoured to define a soft, breathable frame having a pair of eye openings and temple pieces extending from opposite ends of the frame adapted to go around the head of the wearer to hold the frame, in the manner of a face mask, against the eyes of the wearer. Laminated to the fabric frame and overlying the eye openings is a fabric scrim which acts as a light-permeable screen to reduce the intensity of light passing through these openings, thereby preventing glare without however interfering with vision.

9 Claims, 1 Drawing Sheet

LENSLESS SAFETY SUNGLASSES

BACKGROUND OF INVENTION

1. Field of Invention

This invention relates generally to sunglasses, and more particularly to lensless safety sunglasses formed entirely of fabric material adapted to reduce glare without impairing vision.

2. Status of Prior Art

Conventional sunglasses are eyeglasses having tinted =or polarizing lenses which protect the eyes of the wearer from the sun's glare. A typical pair of sunglasses includes a rigid frame formed of metal or plastic whose eye openings are each provided with a bezel in which a lens is mounted. Hinged to opposite sides of this frame are temple pieces which go over the ears of the wearer to support the frame adjacent the eyes. The degree of protection depends on the lenses, for darkly tinted lenses afford greater protection than lightly tinted lenses.

Though conventional sunglasses serve to reduce glare, tennis players and other athletes who play outdoors usually elect not to wear sunglasses. The reason athletes may refuse to wear sunglasses even though they are disturbed in the course of play by the sun's glare is because of the safety factor. Should a tennis or other play ball strike the sunglasses, it may shatter the frame or the lenses, with possibly serious consequences.

Another factor which discourages an athlete from wearing sunglasses is that they are easily dislodged from the head of the wearer. All that holds these sunglasses in place are their temple pieces which go over the ears; hence a vigorous head movement in the course of play may cause the sunglasses to fall off the head. Yet another factor which militates against the use of sunglasses is that their transparent plastic or glass lenses are somewhat reflective, depending on the angle of incident light rays. Reflection from these lenses may in some instances impair vision. Still another negative factor is the lenses of conventional sunglasses may become cloudy as a result of mist formed on the surface of the lenses when the wearer is perspiring heavily.

When the sun is so bothersome that a tennis player simply must wear sunglasses, for reasons of safety, he will then wear over the sunglasses, clear sport goggles. But such goggles tend to fog up as a result of perspiration, and then impair the player's vision. Moreover, it may not be comfortable to wear sport goggles over sunglasses.

Inasmuch as lensless safety sunglasses in accordance with the invention include a soft frame formed of fabric sheeting having eye openings therein, which frame is secured to the head of the wearer, to this extent they are similar to a fabric face mask having eye openings. Of prior art interest therefore is the Rudo U.S. Pat. No. 3,354,884 showing a face mask.

And since lensless safety sunglasses in accordance with the invention make use of a fabric scrim as a screen to reduce glare, which scrim creates myriad fine holes, also of prior art interest is the sun screening glasses disclosed in the Smith U.S. Pat. No. 4,955,709. In the Smith patent, the lenses of the sun screening glasses are formed of metal or opaque plastic plates perforated to create a cluster of clolsely-spaced small holes. These holes afford the wearer with some vision while shielding the eyes from direct light or glare.

The Byler U.S. Pat. No. 3,967,885 discloses eyeglasses for post operative cataract patients in which the eye openings in a spectacles frame are covered by a perforated mask to protect the eyes against excessive light.

The LeMay U.S. Pat. No. 5,488,510 shows an optical viewing device for television which is attachable by straps to the head of the viewer. The device is provided with a front window covered by a mesh screen which is said to afford depth enhancement when viewing a TV screen.

SUMMARY OF INVENTION

In view of the foregoing, the main object of this invention is to provide lensless sunglasses that act to reduce glare without interfering with vision, which sun glasses are soft and unbreakable and therefore can be worn safely and comfortably by athletes.

More particularly, an object of this invention is to provide sunglasses of the above type formed entirely of fabric material, the fabric frame of the sunglasses having eye openings screened by a fabric scrim which acts to reduce the intensity of light passing through the eye openings to prevent glare.

A salient feature of the invention is that the glare-reducing, light-permeable fabric scrim, unlike lenses, is non-reflective and does not interfere with the wearer's vision. Also fabric sunglasses in accordance with the invention are breathable and do not cloud over as a result of perspiration.

A further object of the invention is to provide safety sunglasses of the above type which are firmly secured to the wearer's head and cannot be dislodged therefrom even in the course of vigorous play.

Briefly stated, these objects are attained by lensless safety sunglasses formed of fabric material die cut or otherwise contoured to define a soft, breathable frame having a pair of eye openings and temple pieces extending from opposite ends of the frame adapted to go around the head of the wearer to hold the frame, in the manner of a face mask, against the eyes of the wearer. Laminated to the fabric frame and overlying the eye openings is a fabric scrim which acts as a light-permeable screen to reduce the intensity of light passing through these openings, thereby preventing glare without however interfering with vision.

BRIEF DESCRIPTION OF DRAWING

For a better understanding of the invention as well as other objects and further features thereof, reference is made to the following detailed description to be read in conjunction with the accompanying drawings, wherein.

DESCRIPTION OF INVENTION

Figure 1:
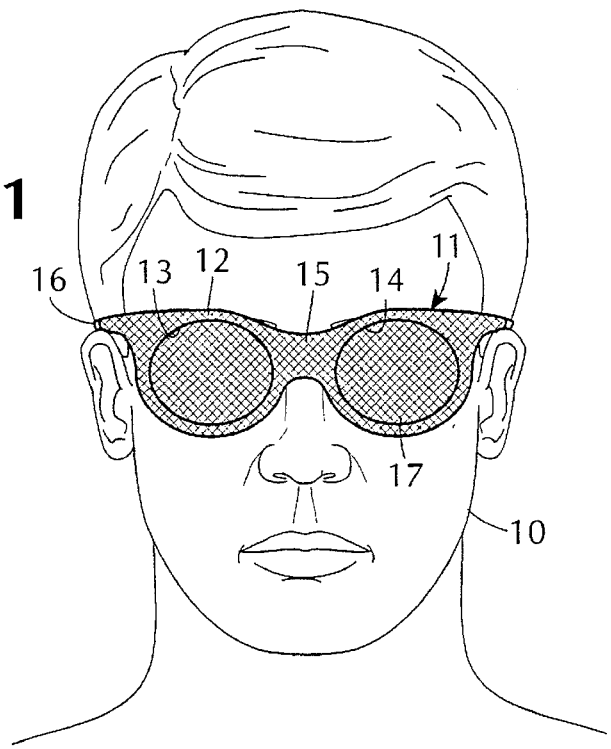
FIG. 1 shows lensless safety sunglasses in accordance with the invention applied to the head of a wearer.
Figure 2:
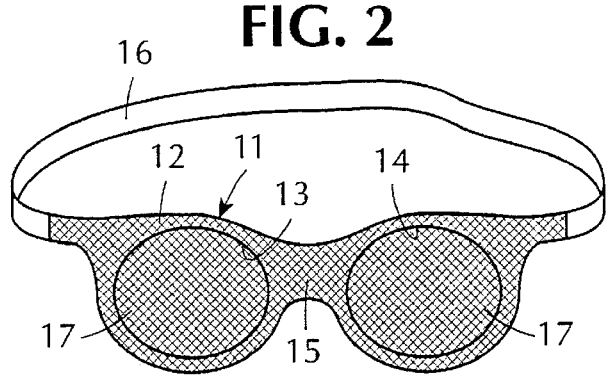
FIG. 2 shows one preferred embodiment of the sunglasses.
Figure 3:
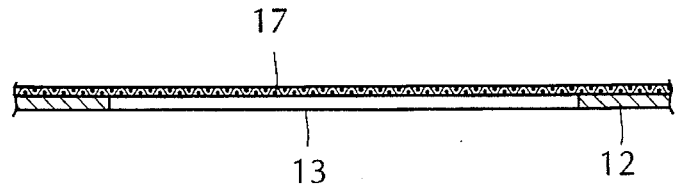
FIG. 3 is a section taken through the frame of the sunglasses.

Referring now to FIGS. 1 and 2, there is shown in these figures the head 10 of an individual wearing lensless safety sunglasses 11 in accordance with the invention.

sunglasses 11 include a soft frame 12 formed of fabric sheeting made of natural or synthetic fibers, such as cotton, wool, nylon or polyethylene. The fabric may be of woven or non-woven construction and is breathable and moisture-absorbent so that when the sunglasses are worn by a perspiring athlete, moisture from the forehead is absorbed by the frame whose upper edge engages the brow. For this purpose the fabric forming the frame may be texturized or be of Terry cloth or similar absorbent soft fabric.

The fabric sheeting is die cut or otherwise contoured to define a frame having eye openings 13 and 14 and a midsection 15 bridging these openings adapted to rest on the nose bridge of the individual, so that the upper edge of the frame engages the brow above the eyes.

Sewn or otherwise joined to opposite ends of fabric frame 12 is a band 16 of elastic material such as SPANDEX to create a loop which is stretchable to go over and behind. the head of the individual to draw frame 12 against the eyes with the eye, openings in registration therewith in the manner of a face mask.

Laminated to the outer surface of fabric frame 12 is a sheet 17 of fabric scrim material whose shape corresponds to that of the frame so that the eye openings 13 and 14 in the frame are screened by the scrim material to filter the light passing through these openings. It is important to note that when a mesh or screen is held close to the eyes, the eyes do not see the mesh but only the openings therein.

A conventional scrim is a loosely woven fabric which because of its myriad fine pores is effectively transparent. A scrim is often used as a drop in a theater to create special effects or atmosphere. Thus when a scrim is dropped before a stage occupied by a brightly illuminated stage set and actors wearing vividly colored costumes, what the audience then sees clearly through the scrim is a softly lit stage in which the lighting of the set and of the actors is subdued.

A light-permeable scrim 17 in accordance with the invention may be derived from woven fine silk having minute openings at the interstices of the fibers. Or the scrim may be woven of fine thermoplastic fibers which are thermally bonded at their points of intersection to maintain the dimensions of the fine pores. The fibers forming the scrim are preferably dull or non-reflective so that the scrim effectively has a matte finish and does not reflect light impinging on the scrim, but only passes light through the scrim to an extent determined by its screening or light filtering properties.

The degree to which the weave of the scrim is open determines its light-permeability characteristics, for the weave fixes the size of the light holes. Thus a relatively open scrim weave produces larger light holes than a tighter weave. Hence by the choice of scrim weave one can produce a range of lensless sunglasses equivalent to those having lightly-tinted, moderately-tinted and darkly-tinted lenses.

Hence scrim 17 screens the eye openings in the frame to reduce the amount of light passing therethrough to prevent glare and minimize reflectivity. But the scrim does not impair vision and the wearer of the lensless sunglasses sees clearly under somewhat reduced lighting conditions. In very bright sunlight, the wearer sees better with the lensless sunglasses than he does without them.

Because the lensless sunglasses are strapped to the head by the elastic band, the sunglasses will not be displaced however vigorously the wearer moves. Yet it is a simple matter to don or remove the sunglasses. And in practice the fabric sunglasses may be multi-colored or otherwise decorated to become a fashion accessory.

It is not necessary that the scrim have the same dimensions and shape as the frame, for in practice the scrim for screening each eye opening may be a round disc adhered to the fabric region surrounding the eye opening.

And it is not necessary that the frame have the shape shown in the figures, for just as conventional eyeglasses have frames in a wide range of different shapes, the frames of the lensless sunglasses may have a great variety of different shapes.

Because the porous fabric forming the frame is liquid-absorbent and breathable, and the scrim covering the eye openings is both light-permeable and moisture-permeable, even though the frame is held like a face mask against the eye region of the wearer between the forehead and the nose, perspiration in this region does not interfere with vision, for it is absorbed and dissipated by the frame and the scrim covering the eye openings.

Second Embodiment

The safety sunglasses shown in FIGS. 1 and 2 are made in two pieces, one being the scrim-frame laminate and the other the elastic band whose ends are attached to opposite ends of the frame.

Figure 4:
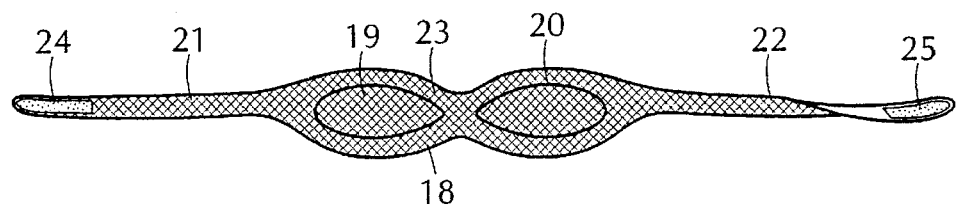
FIG. 4 shows another embodiment of the sunglasses.

In the embodiment of the safety sunglasses shown in FIG. 4 the sunglasses do not have a separate band, for the means to strap the frame to the head of the wearer is integrated with the frame, and the sunglasses are therefore made in one piece.

In this embodiment, a sheeting of fabric material is die-cut to define a frame 18 having a pair of eye openings 19 and 20 and a pair of temple straps 21 and 22 extending from opposite ends of the frame and integral therewith. Laminated to frame 18 and screening the eye openings is a fabric scrim 23.

Bonded to the free end of temple strap 21 is a strip 24 of the hook or male component of a Velcro fabric fastener. And bonded to the free end of temple strap 22 is a strip 25 of the loop or female component of this fastener. Hence. to don the fabric sunglasses, temple straps 21 and 22 are pulled behind the head and are joined together by the Velcro fastener.

The lengths of Velcro strips 24 and 25 are such as to accommodate different head sizes, the degree of overlap of these strips depending on head size.

While there has been disclosed preferred embodiments of lensless safety sunglasses in accordance with the invention, it is to be understood that many changes may be made therein without departing from the spirit of the invention.

I claim:

1. Lensless safety sunglasses attachable to the head of a wearer comprising:

A. a frame formed of fabric material having a pair of eye openings and a midsection between the eye openings contoured to fit on a nose bridge of the wearer;

B. a screen covering each eye opening formed of a light-permeable fabric scrim having myriad minute holes which act to reduce the intensity of light passing through the eye opening; and C. means joined to opposite ends of the frame to secure the sunglasses to the head of the wearer.

2. Sunglasses as set forth in claim 1, in which said frame is formed by die cutting a sheet of fabric material to define a contoured frame having said eye openings and said midsection.

3. Sunglasses as set forth in claim 2, in which said fabric scrim is formed by die-cutting a sheet of scrim material to define a contoured scrim corresponding to said contoured frame and laminated thereto.

4. Sunglasses as set forth in claim 1, in which the fabric forming the frame is moisture absorbent to absorb perspiration from the forehead of the wearer.

5. Sunglasses as set forth in claim 4, in which the absorbent fabric is texturized.

6. Sunglasses as set forth in claim 1, in which the scrim is formed of woven silk.

7. Sunglasses as set forth in claim 1, in which said means is formed by an elastic fabric band the ends of which are secured to the opposite end of the frame.

8. Sunglasses as set forth in claim 1, in which said means are formed by a pair of temple straps joined to the opposite ends of the frame.

9. Sunglasses as set forth in claim 8, in which attached to one of said straps is the male element of a Velcro fastener and attached to the other of said straps is the female element.

* * * * *